(12) United States Patent
Paton et al.

(10) Patent No.: US 6,733,498 B2
(45) Date of Patent: May 11, 2004

(54) SYSTEM AND METHOD FOR CONTROL OF TISSUE WELDING

(75) Inventors: Boris E. Paton, Kiev (UA); Vladimir K. Lebedev, Kiev (UA); Alexei V. Lebedev, Kiev (UA); Yurii A. Masalov, Kiev (UA); Olga N. Ivanova, Kiev (UA); Mykhailo P. Zakharash, Kiev (UA); Yuri A. Furmanov, Kiev (UA)

(73) Assignee: Live Tissue Connect, Inc., Corpus Christi, TX (US)

( * ) Notice: Subject to any disclaimer, the term of this patent is extended or adjusted under 35 U.S.C. 154(b) by 0 days.

(21) Appl. No.: 10/078,828

(22) Filed: Feb. 19, 2002

(65) Prior Publication Data

US 2003/0158551 A1 Aug. 21, 2003

(51) Int. Cl.[7] .............................................. A61B 18/18
(52) U.S. Cl. ............................................ 606/41; 606/49
(58) Field of Search ............................. 606/32, 41, 45, 606/49

(56) References Cited

U.S. PATENT DOCUMENTS

| | | |
|---|---|---|
| 3,980,085 A | 9/1976 | Ikuno |
| 4,418,692 A | 12/1983 | Guay |
| 4,471,787 A | 9/1984 | Bentall |
| 4,492,231 A | 1/1985 | Auth |
| 4,556,051 A | 12/1985 | Maurer |
| 4,633,870 A | 1/1987 | Sauer |
| 4,738,250 A | 4/1988 | Fulkerson et al. |
| 4,892,098 A | 1/1990 | Sauer |
| 5,151,102 A | 9/1992 | Kamiyama et al. |
| 5,158,081 A | 10/1992 | McWhorter et al. |
| 5,190,541 A | 3/1993 | Abele et al. |
| 5,300,065 A | 4/1994 | Anderson |
| 5,336,221 A | 8/1994 | Anderson |
| 5,342,381 A | 8/1994 | Tidemand |
| 5,342,393 A | 8/1994 | Stack |
| 5,364,389 A | 11/1994 | Anderson |
| 5,403,312 A | 4/1995 | Taymor-Luria |
| 5,423,814 A | 6/1995 | Zhu et al. |
| 5,431,645 A | 7/1995 | Smith et al. |
| 5,817,093 A * | 10/1998 | Williamson, IV et al. .... 606/50 |
| 6,033,399 A * | 3/2000 | Gines ........................... 606/38 |
| 6,083,223 A * | 7/2000 | Baker ........................... 606/52 |
| 6,228,080 B1 * | 5/2001 | Gines ........................... 606/34 |

FOREIGN PATENT DOCUMENTS

| | | |
|---|---|---|
| DE | 196 41 563 A1 | 4/1998 |
| EP | 0 703 461 A1 | 9/1995 |
| EP | 0 761 174 A1 | 9/1996 |
| WO | WO 97/10764 | 8/1996 |
| WO | WO 98/38935 | 3/1998 |

OTHER PUBLICATIONS

US 5443463 Aug. 1995 Stern et al.
US 5450845 Sep. 1995 Axelgaard.
US 5507744 Apr. 1996 Tay et al.

(List continued on next page.)

*Primary Examiner*—Linda C. M. Dvorak
*Assistant Examiner*—Aaron Roane
(74) *Attorney, Agent, or Firm*—Charles W. Hanor, P.C.

(57) ABSTRACT

A system and method for welding of biological tissue by applying an RF voltage during a first stage to electrodes of a tissue welding tool; monitoring tissue impedance, and determining a minimum tissue impedance value during the first stage; determining relative tissue impedance; detecting when the relative tissue impedance reaches a predetermined relative tissue impedance value and starting a second stage; calculating the duration of the second stage as a function of the duration of the first stage; and applying the RF voltage during the second stage to the electrodes of the tissue welding tool.

36 Claims, 6 Drawing Sheets

OTHER PUBLICATIONS

US 5558671 Sep. 1996 Yates.
US 5776130 Jul. 1998 Buysse et al.
US 5827271 Oct. 1998 Buysse et al.
"Automatically controlled bipolar electrocoagulation" by Vallfors and Bergdahi, Neurosurgery Rev. 7. (1984), pp. 187–190.
"The mechanism of Blood Vessel Closure by High Frequency Electrocoagulation" by Sigel et al, Surgery. Gynecology & Obstetrics, pp. 823–831, Oct. 1965.
US 5496312 Mar. 15, 1996 Klicek.
US 5443463 Aug. 22, 1995 Stern.
US 4154240 May 1979 Ikuno et al.
US 5954686 Sep. 1999 Garito et al.
US 5562503 Oct. 8, 1996 Ellman et al.
US 5713896 Feb. 1998 Nardella.
US 5718701 Feb. 1998 Shai et al.
US 5476481 Dec. 1995 Schondorf.
US 5817093 Oct. 1998 Williamson IV et al.
US 6086586 Jul. 11, 2000 Hooven.
US 5540684 Jul. 30, 1996 Hassler, Jr.
US 6228080 May 8, 2001 Gines.
US 6245065 Jun. 12, 2001 Panescu et al.
US 5415657 May 16, 1995 Taymor–Luria.

* cited by examiner

SYSTEM AND METHOD FOR CONTROL OF TISSUE WELDING

CROSS-REFERENCE TO RELATED APPLICATIONS

This application is related to U.S. patent application Ser. No. 09/022,869, entitled "Bonding of Soft Biological Tissues by Passing High Frequency Electric Current Therethrough", filed Feb. 12, 1998, the contents of which are incorporated herein by reference.

BACKGROUND OF THE INVENTION

The present invention is related to bonding or welding of soft tissue and, more particularly, to a system and method for controlling tissue welding.

RF electrosurgical tools are widely used in a variety of medical applications for cutting, soft tissues, hemostasis and various cauterization procedures. Currently-available electrosurgical bipolar instruments generally use two electrodes of opposite polarity, one of which is located on each of the opposite jaws of, for example, a grasper. In use, tissue is held between the electrodes and alternating RF current flows between the two electrodes, heating the tissue. When the tissue temperature reaches about 50–55° C., denaturation of albumens occurs in the tissue. The denaturation of the albumens results in the "unwinding" of globular molecules of albumen and their subsequent entangling which results in coagulation of the tissues. Once the tissue is treated in this way, the tissue can be cut in the welded area with no bleeding. This process is commonly referred to as bipolar coagulation.

Tissue welding generally comprises bringing together edges of an incision to be bonded, compressing the tissue with a bipolar tool and heating the tissue by the RF electric current flowing through them. One of the major differences between tissue welding procedures and coagulation with the purpose of hemostasis is that tissue welding requires conditions which allow for the formation of a common albumen space between the tissue to be bonded before the beginning of albumen coagulation. If such conditions are not present, coagulation will take place without a reliable connection being formed.

Problems which can occur during the tissue welding process include thermal damage to adjacent structures, over-heating of tissue and under-coagulation. Over-heating of tissue results in delayed healing, excessive scarring, tissue charring/destruction, and in tissue sticking to the electrosurgical tool. If tissue sticks to the electrosurgical tool upon removal, the tissue can be pulled apart at the weld site, adversely affecting hemostasis and causing further injury. Under-coagulation can occur if insufficient energy has been applied to the tissue. Under-coagulation results in weak and unreliable tissue welds, and incomplete hemostasis.

Precise control of the welding process while avoiding excessive thermal damage, over-heating or under-coagulation is a difficult process, particularly when attempting to weld tissue of varying structure, thickness and impedance. The problem of crating a viable automatic control system is particularly important for welding whose purpose is recovery of physiological functions of the organs operated on. After hemostasis, vessels or vascularized tissue parts which have been heated typically do not recover and lose functionality.

Prior attempts to automate the control of tissue coagulation have met with limited success. Attempts to avoid over-heating include the use of electrosurgical tools with built-in temperature measuring devices. Built-in temperature measuring devices are used to measure the tissue temperature, provide feedback and thereby, prevent over-heating. However, use of built-in temperature sensors causes the electrosurgical tools to be cumbersome, while providing only limited or inaccurate information about the status of the inner layers of the tissue between the electrodes where a connection is potentially being formed.

Several prior art references suggest various methods of using the tissue impedance and a minimum tissue impedance value to define a point when coagulation is completed and tissue heating should be discontinued. Other references suggest use of a relationship between tissue impedance and current frequency to detect a point of coagulation.

The prior art methods, however, do not provide effective tissue bonding solutions for use in surgical procedures and specifically lack the ability to adapt to varying tissue types and thickness during the welding procedure.

It would therefore be desirable to provide an electrosurgical system and method suitable both for tissue bonding and for hemostasis which allows for adaptation to varying tissue types, structure, thickness, and impedance without over-heating, while providing a reliable tissue connection. Such a system and method would significantly reduce the time needed for surgical procedures involving tissue welding by eliminating the need for equipment adjustment during the welding process.

BRIEF DESCRIPTION OF THE SEVERAL VIEWS OF THE DRAWINGS

The foregoing summary, as well as the following detailed description of preferred embodiments of the invention, will be better understood when read in conjunction with the appended drawings. For the purpose of illustrating the invention, there is shown in the drawings embodiments which are presently preferred. It should be understood, however, that the invention is not limited to the precise arrangements and instrumentalities shown. In the drawings.

DETAILED DESCRIPTION OF THE INVENTION

The present invention may be applied in a variety of medical procedures involving the joining or bonding of tissue, to produce both strong tissue welds and minimize thermal damage to surrounding tissue, that would otherwise result in delayed wound healing. The system and method of the present invention also provide for automatic adaptation and control of tissue welding and coagulation processes for tissue of varying structure, thickness and/or impedance, without the need for equipment adjustment during the welding and coagulation processes.

Figure 1:
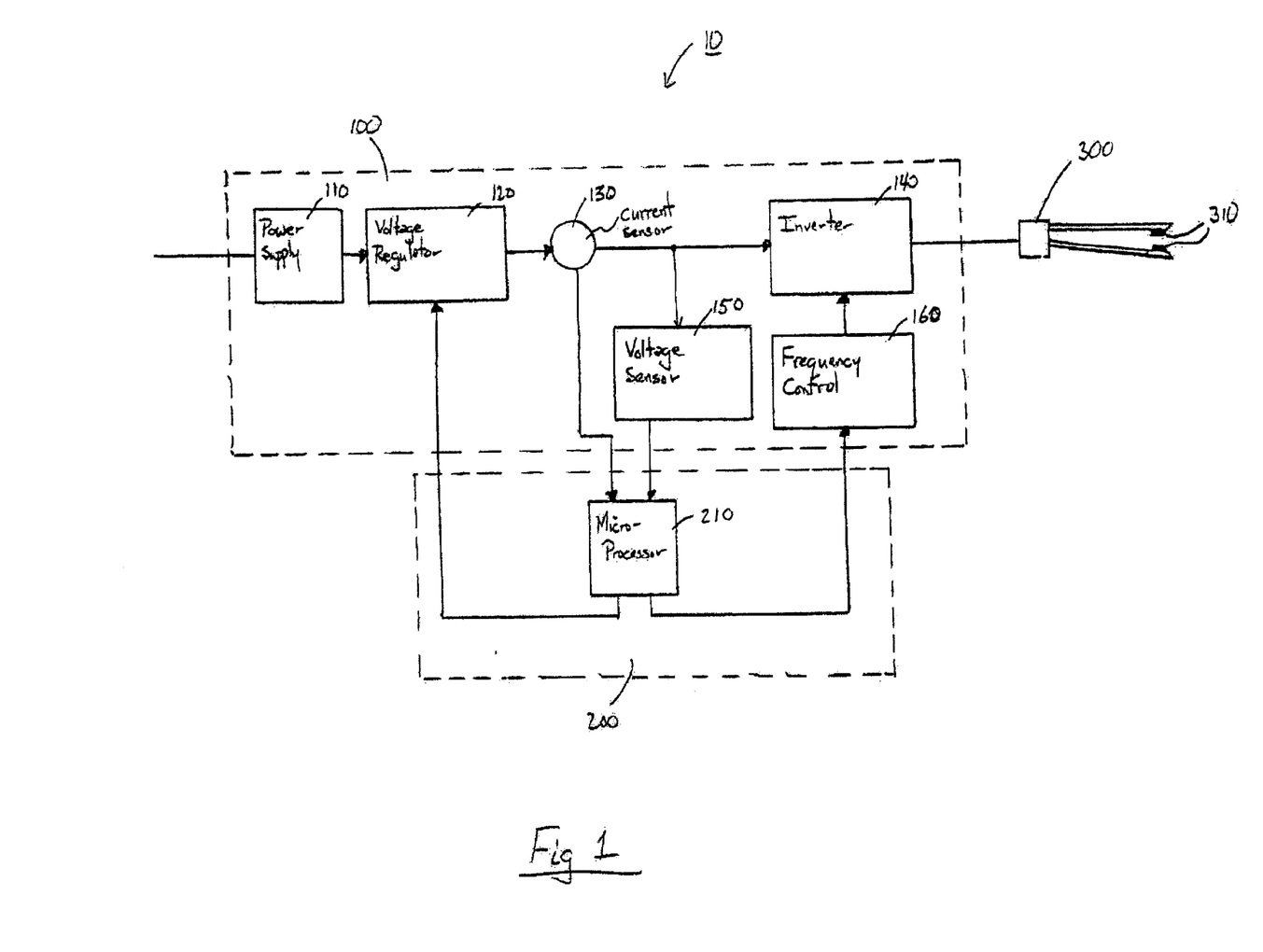
FIG. 1 is a block diagram illustrating one embodiment of the invention.

FIG. 1 illustrates one embodiment of the apparatus 10 of the invention including a power source 100 coupled to electrodes 310 of surgical instrument 300. The power source is preferably adapted to provide RF voltage to the electrodes 310. The power source 100 preferably also comprises one or more sensors for sensing the RF voltage and current between the electrodes 310. As shown in FIG. 1, the sensors preferably include a current sensor 130 and a voltage sensor 150. The apparatus 10 further comprises a control device 200. The control device 200 preferably includes a microprocessor 210 for controlling the power source 100 to provide an RF voltage to the electrodes 310 of the surgical instrument 300. Although the control device 200 is shown with a microprocessor, the control device 200 could include any other type of programmable device, implemented as a microcontroller, digital signal processor, or as a collection of discrete logic devices. The apparatus 10 may also include an actuation device (not shown) coupled to the control device 200 for actuating control device 200 and power source 100. The apparatus 10 may also include a control panel or display (not shown) as a user interface.

The control device 200 is preferably adapted to: control the power source 100 to provide the RF voltage to the electrodes 310 during a first stage; monitor the tissue impedance of tissue between the electrodes 310; determine a minimum tissue impedance value; determine a relative tissue impedance as a ratio of the measured tissue impedance and the minimum tissue impedance value; detect when the relative tissue impedance reaches a predetermined relative tissue impedance value during the first stage (the predetermined relative tissue impedance value being preset or calculated as a function of the RF voltage variation during the first stage); and control the power source to provide an RF voltage during a second stage.

Figure 2:
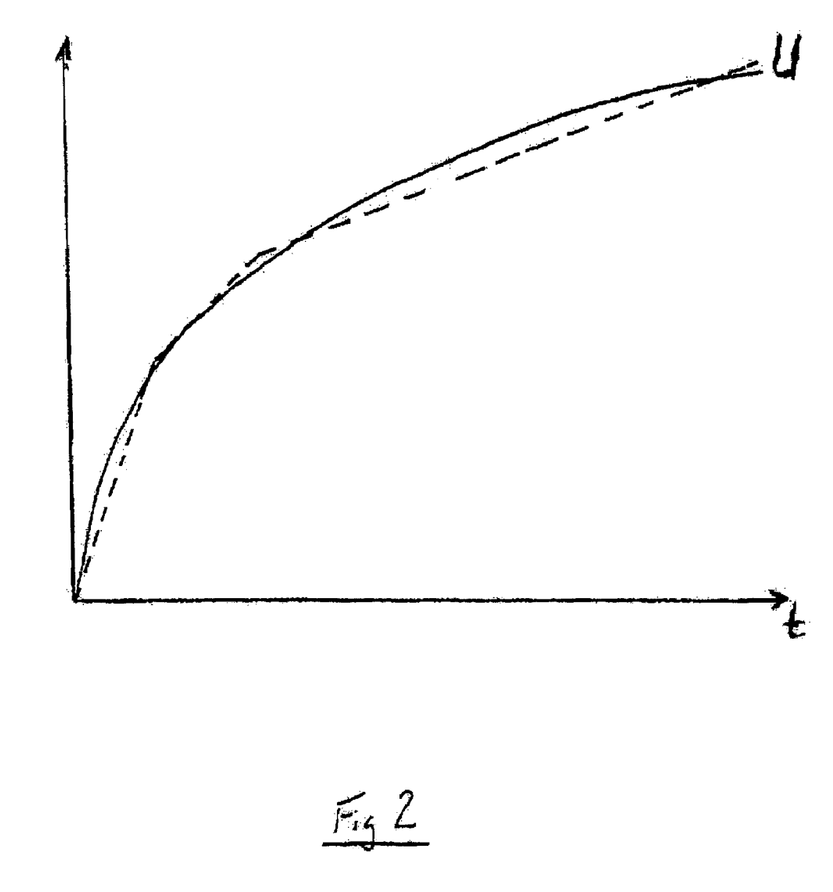
FIG. 2 shows a plot of the voltage applied during the first stage as a function of time for one embodiment of the invention.

The control device 200 preferably controls the power source 100 to provide the RF voltage during the first stage such that the RF voltage increases at a gradually decreasing rate (e.g. a decreasing rate of increase of the RF voltage over time). In one preferred embodiment, the RF voltage increases according to the following equation:

$$U = u_s * t^k$$

where U is voltage, $u_s$ is a constant, t is time, and k is a constant, and where k<1. FIG. 2 shows a plot of the gradually increasing RF voltage (U) provided during the first stage. Varying the RF voltage as described above allows for automatic adjustment of the welding process when tissue of varying thickness and/or physical properties is encountered.

The control device 200 can also be designed to control the power source 100 to provide an approximation of the gradually increasing RF voltage provided during the first stage. The approximation is shown in FIG. 2 as a dashed line comprising a plurality of linear segments.

The control device 200 preferably calculates tissue impedance Z as a function of time by dividing the RF voltage by the electric current, determines and stores a minimum tissue impedance value $Z_{min}$, and then calculates a relative tissue impedance z as a function of time by dividing tissue impedance Z by the minimum tissue impedance value $Z_{min}$. The control device 200 preferably uses a predetermined relative tissue impedance value or calculates a relative tissue impedance value, at which point the first stage is terminated (shown in FIGS. 3, 5, and 6 as value A). The relative tissue impedance value at which the first stage is terminated, hereinafter referred to as the "predetermined" relative tissue impedance value, when calculated, is preferably calculated as a function of the RF voltage during the first stage (e.g. the greater the RF voltage, the lower the calculated, predetermined relative tissue impedance value). The predetermined relative tissue impedance value is preferably within the range of about 1–1.5. When the control device 200 controls the power source 100 to provide an approximation of the RF voltage during the first stage, the predetermined relative tissue impedance value is preferably calculated or set for each segment.

The control device 200 preferably also calculates the RF voltage provided during the second stage as a function of the value of the RF voltage provided during the first stage when the relative tissue impedance reaches the predetermined relative tissue impedance value. The amplitude of the RF voltage provided during the second stage is preferably between about 50–100% of the value of the RF voltage provided at the end of the first stage (i.e. when the relative tissue impedance reaches the predetermined relative tissue impedance value).

Figure 3:
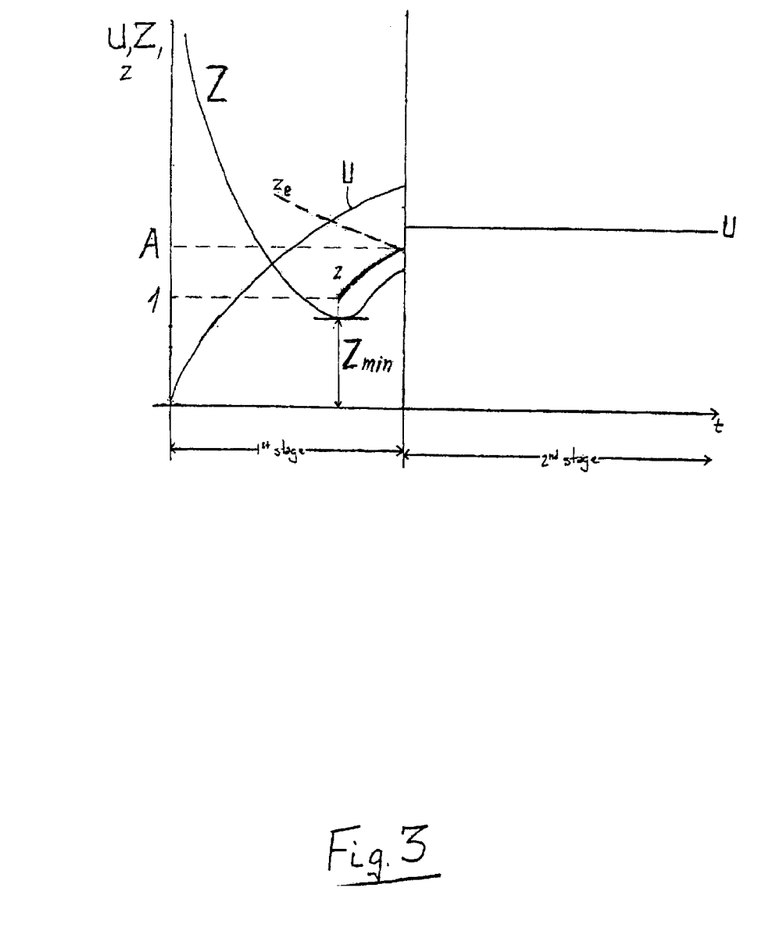
FIG. 3 shows a plot of the voltage, tissue impedance and relative tissue impedance during the first and second stages as a function of time for another embodiment of the invention.

In one preferred embodiment, illustrated in FIG. 3, the control device 200 preferably controls the power source 100 to substantially stabilize the RF voltage provided during the second stage. The duration of the second stage is preferably calculated by the control device 200 as a function of the duration of the first stage.

The control device 200 preferably also controls the power source 100 to modulate the RF voltages provided during the first and second stages by pulses. The pulses are preferably square pulses and have a frequency of between about 100 Hz–60 kHz and a duty cycle of between about 10–90%. A high frequency is preferably selected to prevent cell membranes from recovering during the interval between pulses. The frequency of the pulses may also be varied during the first and second stages.

Figure 4:
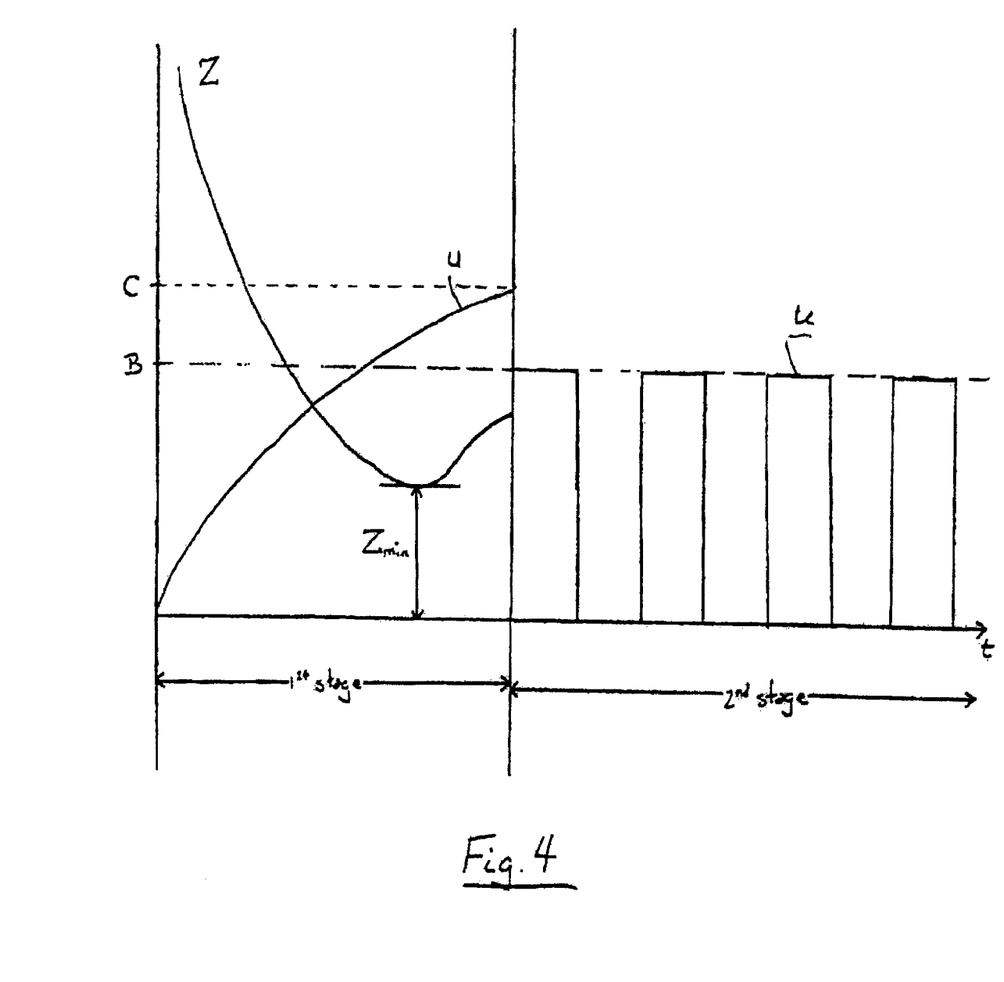
FIG. 4 shows a plot of the voltage and tissue impedance during the first and second stages as a function of time for another embodiment of the invention.

In an alternative embodiment, illustrated in FIG. 4, the control device 200 is designed to control the power source 100 to modulate the RF voltages applied during the first and second stages as described above with pulses having a frequency of between about 100 Hz–60 kHz, and further modulate the RF voltage applied during the second stage with low frequency pulses with a frequency of less than about 100 Hz. The low frequency pulses are preferably square pulses. More preferably, the control device 200 controls the power source 100 to substantially stabilize the amplitude of the RF voltage applied during the second stage. The control device 200 preferably calculates the duration of the second stage as a function of the duration of the first stage.

The amplitude of the RF voltage applied during the second stage, shown in FIG. 4 as B, is preferably calculated as a function of the value of the RF voltage applied at the end of the first stage (shown in FIG. 4 as C).

The frequency of the low frequency pulses further modulating the RF voltage during the second stage is preferably defined as a function of the duration of the first stage. More preferably, the frequency of the low frequency pulses is defined such that there are between about 5–10 pulses during the second stage.

Figure 5:
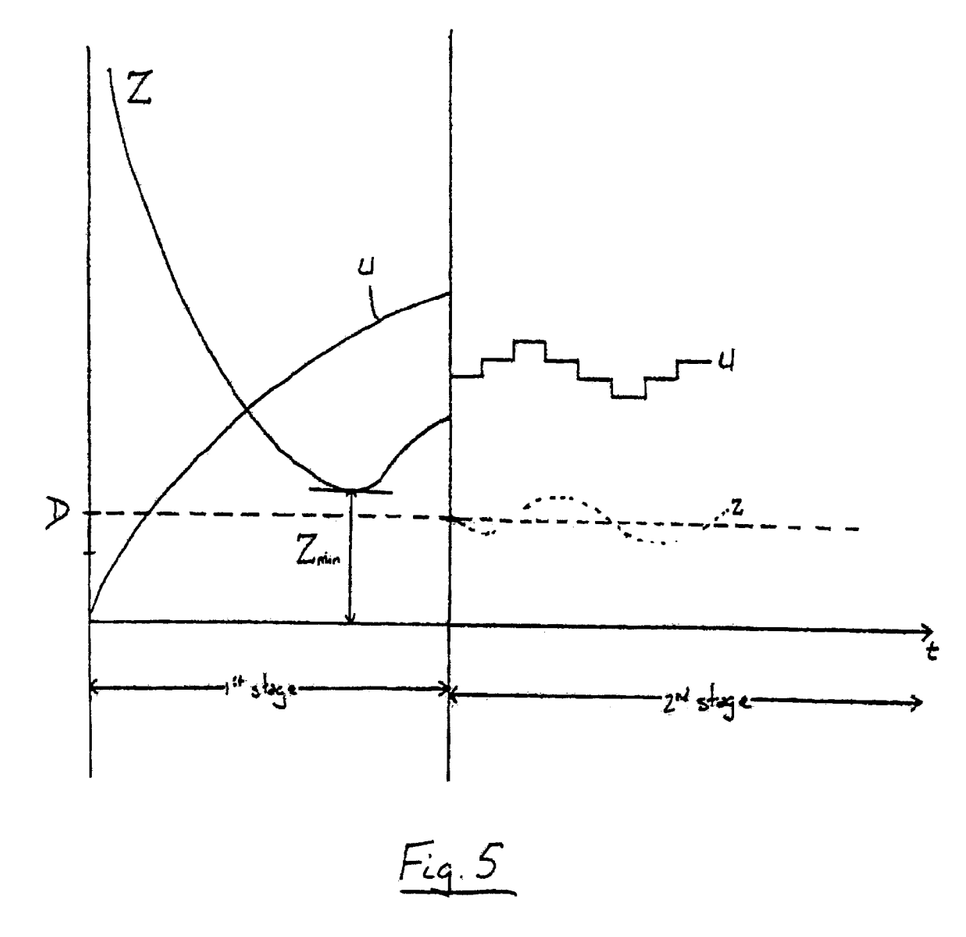
FIG. 5 shows a plot of the voltage, tissue impedance and relative tissue impedance during the first and second stages as a function of time for another embodiment of the invention.

In another alternative embodiment, illustrated in FIG. 5, the control device 200 controls the power source to vary the RF voltage provided during the second stage as a function of the relative tissue impedance z. Preferably, the control device 200 controls the power source 100 to provide the RF voltage during the second stage to substantially stabilize the relative tissue impedance z at a relative tissue impedance level reached at the end of the first stage (shown in FIG. 5 as A). More specifically, the control device 200 is preferably designed to control the power source 100 to vary the RF voltage provided during the second stage as a function of the relative tissue impedance z by reducing the RF voltage when the relative tissue impedance z is greater than the predetermined relative tissue impedance value and increasing the RF voltage when the relative tissue impedance z is less than the predetermined relative tissue impedance value. Alternatively, the control device 200 can control the power source 100 to provide RF voltage during the second stage to vary the relative tissue impedance according to a preset program. The control device 200 preferably also calculates the duration of the second stage as a function of the duration of the first stage.

Figure 6:
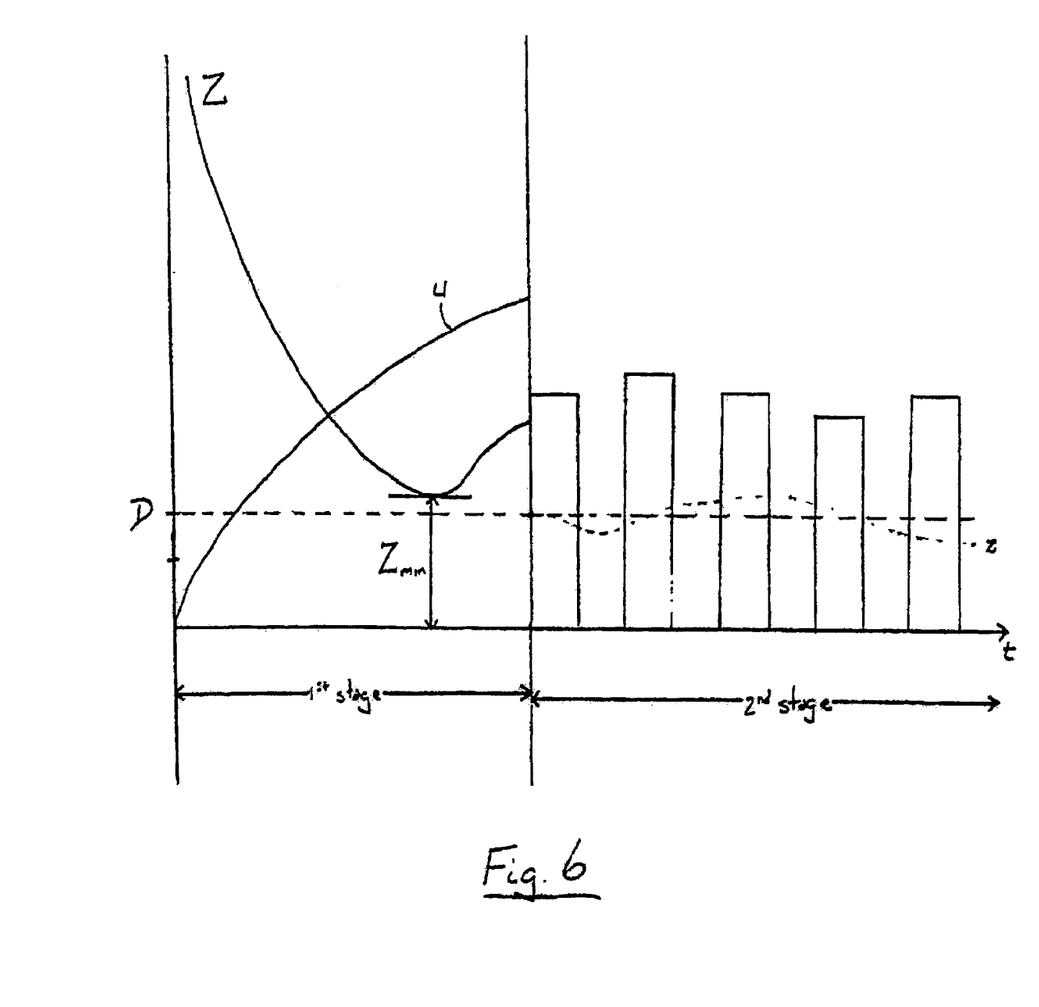
FIG. 6 shows a plot of the voltage, tissue impedance and relative tissue impedance during the first and second stages as a function of time for another embodiment of the invention.

In another alternative embodiment illustrated in FIG. 6, the control device 200 is designed to control the power source 100 to modulate the RF voltage provided during the first and second stages with pulses having a frequency of between about 100 Hz–60 kHz, and further modulate the RF voltage provided during the second stage with low frequency pulses. The control device 200 controls the power source 100 to provide the RF voltage during the second stage to substantially stabilize the relative tissue impedance z at a relative tissue impedance level reached at the end of the first stage (shown in FIG. 6 as A). Alternatively, the control device 200 can control the power source 100 to provide RF voltage during the second stage to vary the relative tissue impedance according to a preset program. The control device 200 preferably also calculates the duration of the second stage as a function of the duration of the first stage.

In each of the above embodiments the control device 200 preferably can be set to regulate the modulation pulse frequency to within about 100 Hz–60 kHz to provide a minimum tissue resistance. Preferably, regulatory methods known in the art of external systems are used. The control device 200 also preferably regulates the duty cycle of the modulation pulses during tissue welding such that energy consumption for tissue breakdown and heating is reduced or minimized. Preferably, regulatory methods known in the art of external self-adjusting systems are used.

The control device 200 is also preferably capable of controlling the power source 100 to provide modulated pulse bursts of the RF voltage to the electrodes during the intervals between welding sessions. The duration of a pulse burst is preferably within about 2–15 msec. The frequency of the pulse bursts is preferably within about 3–15 Hz. Tissue welding is preferably actuated if the average tissue resistance of tissue between the electrodes is less than a preset value.

The control device 200 is also preferably capable of calculating during welding a temperature of the electrodes, a temperature of the tissue engaged between the electrodes, and a degree of tissue coagulation, for example, using a mathematical model and based on known values of the electric current and RF voltage. The calculated values are preferably used to adjust the RF voltage increase rate during the first stage and the duration of tissue welding. Adjustment of the RF voltage increase rate and the duration of tissue welding is preferably performed using algorithms known in the art of control systems. Preferably, known tissue coagulation models are used as a model. Adjustment is preferably carried out within about +/- 15% of the set voltage increase rate and welding duration.

The frequency of the low frequency pulses, when modulating the RF voltage provided during the second stage, is preferably defined as a function of the duration of the first stage. More preferably, the frequency of the low frequency pulses is defined such that there are between about 5–10 pulses during the second stage.

Preferably, the control device 200 further comprises a regulatory system (not shown) for stabilizing or varying the relative tissue impedance z according to a preset program. Specifically, the regulatory system stabilizes or varies the relative tissue impedance z by varying the RF voltage by a predetermined amount, the RF voltage being varied based on the direction of change of the relative tissue impedance z.

The control device 200 preferably further comprises apparatus for monitoring tissue welding, and stopping tissue welding and providing a signal to a user if the RF voltage applied during the first stage reaches a preset RF voltage level and/or if the relative tissue impedance fails to reach the predetermined relative tissue impedance value.

The control device 200 preferably further comprises apparatus for monitoring tissue welding, and stopping tissue welding and providing a signal to a user when the tissue impedance reaches a short circuit impedance of the electrodes of the tissue welding tool.

The control device 200 preferably further comprises apparatus for monitoring tissue welding and providing a signal to a user when tissue welding is completed at the end of the second stage. The signal is preferably provided after a time lag needed for the welded tissue to cool off.

The control device 200 also preferably turns off the RF voltage and provides a corresponding signal to the user when the tissue impedance or the duration of welding exceeds threshold parameters.

The control device 200 preferably further comprises a filter for filtering the tissue impedance values. The control device 200 can also be designed to control the duration of the first stage as a function of the relative tissue impedance.

In one embodiment of the method for welding of biological tissue of the present invention, the method comprises: applying an RF voltage during a first stage to electrodes of a tissue welding tool; monitoring tissue impedance, and determining a minimum tissue impedance value during the first stage; determining relative tissue impedance; detecting when the relative tissue impedance reaches a predetermined relative tissue impedance value; starting a second stage when the relative tissue impedance reaches the predetermined relative tissue impedance value; calculating the duration of the second stage as a function of the duration of the first stage; and applying the RF voltage during the second stage to the electrodes of the tissue welding tool.

The relative tissue impedance is preferably calculated as the ratio of tissue impedance to the minimum tissue impedance value. The RF voltage applied during the first stage preferably increases at a gradually decreasing rate, preferably according to the following equation:

$$U = u_s * t^k$$

where U is voltage, $u_s$ is a constant, t is time, and k is a constant, and where k<1.

Monitoring tissue impedance preferably includes measuring the RF voltage and electric current between the electrodes of the tissue welding tool and calculating tissue impedance by dividing the voltage by the electric current.

The predetermined relative tissue impedance value is preferably a predetermined or preset value or is determined as a function of the RF voltage applied during the first stage. The predetermined relative tissue impedance value is preferably within the range of about 1–5.

The RF voltage applied during the second stage is preferably calculated as a function of the value of the RF voltage applied at the end of the first stage (i.e. when the relative tissue impedance reaches the predetermined relative tissue impedance value). The RF voltage applied during the second stage is preferably between about 50–100% of the value of the RF voltage applied at the end of the first stage.

In one preferred embodiment of the method of the present invention, applying the RF voltage during the second stage comprises substantially stabilizing the RF voltage applied. FIG. 3 illustrates the method by showing a plot of the RF voltage applied during the first and second stages, the tissue impedance Z and the relative tissue impedance z. As shown in FIG. 3, the RF voltage applied during the first stage is gradually increased until the relative tissue impedance z reaches a predetermined relative tissue impedance value, shown in FIG. 3 at A. As discussed above, the predetermined relative tissue impedance value can be preset or determined as a function of the RF voltage applied during the first stage. When the relative tissue impedance reaches the predetermined relative tissue impedance value, a substantially stabilized RF voltage is applied during the second stage. The RF voltages applied during the first and second stages are preferably modulated by pulses. The pulses preferably substantially square and have a frequency of between about 100 Hz–60 kHz and a duty cycle of between about 10–90%. The frequency of the pulses can be varied during the first and second stages.

In an alternative embodiment of the method of the present invention, the RF voltages applied during the first and second stages are modulated with pulses having a frequency of between about 100 Hz–60 kHz, and the RF voltage applied during the second stage is further modulated with low frequency pulses. FIG. 4 illustrates the method, showing a plot of the RF voltage applied during the second stage modulated by low frequency pulses. Preferably, the amplitude of the RF voltage applied during the second stage is substantially stabilized at a level shown in FIG. 4 as B. The amplitude of the RF voltage is preferably calculated as a function of the value of the RF voltage applied at the end of the first stage (shown in FIG. 4 as C).

The low frequency pulses are preferably substantially square pulses. The frequency of the low frequency pulses modulating the RF voltage applied during the second stage is preferably defined as a function of the duration of the first stage. More preferably, the frequency of the low frequency pulses is defined such that there are between about 5–10 pulses during the second stage.

In another alternative embodiment of the method of the present invention, the RF voltage applied during the second stage is varied as a function of the relative tissue impedance. FIG. 5 illustrates the method, showing a plot of the RF voltage and relative tissue impedance applied during the second stage.

Preferably the RF voltage applied during the second stage is varied as a function of the relative tissue impedance by reducing the RF voltage when the relative tissue impedance is greater than the predetermined relative tissue impedance value and increasing the RF voltage when the relative tissue impedance z is less than the predetermined relative tissue impedance value. More preferably, the relative tissue impedance is substantially stabilized at a relative tissue impedance level reached at the end of the first stage. Alternatively, the RF voltage applied during the second stage can be varied so as to vary the relative tissue impedance according to a preset program.

In another alternative embodiment of the method of the present invention, illustrated in FIG. 6, the RF voltages applied during the first and second stages are modulated with pulses having a frequency of between about 100 Hz–60 kHz, the RF voltage applied during the second stage are further modulated with low frequency pulses, and the relative tissue impedance is substantially stabilized at a relative tissue impedance level reached at the end of the first stage. Alternatively, the RF voltage applied during the second stage can be varied so as to vary the relative tissue impedance according to a preset program.

The low frequency pules are preferably square pules. The frequency of the low frequency pulses is preferably defined as a function of the duration of the first stage. More preferably, the frequency of the low frequency pulses is defined such that there are between about 5–10 pulses during the second stage. Stabilizing the relative tissue impedance is preferably performed by a regulatory system by varying the RF voltage by a predetermined amount or one step, the sign of the RF voltage change being opposite to the sign of the relative tissue impedance change.

The method of each of the above embodiments preferably further comprises monitoring tissue welding, and stopping tissue welding and providing a signal to a user if the RF voltage applied during the first stage reaches a preset RF voltage level and/or if the relative tissue impedance fails to reach the predetermined relative tissue impedance value.

Preferably the methods of the above embodiments further comprise monitoring tissue welding and stopping tissue welding and providing a signal to a user when the tissue impedance reaches a short circuit impedance of the electrodes of the tissue welding tool.

Preferably the methods of the above embodiments further comprise monitoring tissue welding and providing a signal to a user when tissue welding is completed at the end of the second stage. The signal is preferably provided after a time lag needed for the welded tissue to substantially cool off.

Preferably the methods of the above embodiments further comprise monitoring tissue welding and stopping tissue welding and providing a signal to a user when the tissue impedance or the duration of welding exceeds threshold parameters.

In another embodiment of the present invention, a control method is provided for welding of biological tissue comprising: applying an increasing RF voltage, preferably increasing at a gradually decreasing rate, to the electrodes of a tissue welding tool during a first stage; measuring the values of the RF voltage and electric current passing through the tissue, and the duration of the first stage; calculating tissue impedance values by dividing the RF voltage values by the electric current values; determining a minimum tissue impedance value; storing the minimum tissue impedance value; calculating relative tissue impedance values by dividing the values of the tissue impedance by the minimum tissue impedance value; stopping the first stage when the relative tissue impedance reaches an endpoint relative tissue impedance value calculated as a function of the relative tissue impedance; storing the duration of the first stage and a value of the RF voltage at the end of the first stage (i.e. when the relative tissue impedance reaches the endpoint relative tissue impedance value); calculating an RF voltage level for a second stage as a function of the value of the RF voltage at the end of the first stage; calculating the duration of the second stage as a function of the duration of the first stage; and applying an RF voltage during the second stage at the RF voltage level calculated above.

In another embodiment of the present invention, a control method is provided for welding of biological tissue comprising: applying an increasing RF voltage, preferably increasing at a gradually decreasing rate, to the electrodes of a tissue welding tool during a first stage; measuring the values of the RF voltage and electric current passing through the tissue, and the duration of the first stage; calculating tissue impedance values by dividing the RF voltage values by the electric current values; determining a minimum tissue impedance value; storing the minimum tissue impedance value; calculating a relative tissue impedance value by dividing the tissue impedance values by the minimum tissue impedance value; stopping the first stage when the relative tissue impedance reaches an endpoint relative tissue impedance value calculated as a function of the relative tissue impedance; storing the duration of the first stage and the RF voltage at the end of the first stage; calculating an RF voltage level for a second stage as a function of the value of the RF voltage at the end of the first stage; calculating the duration of the second stage as a function of the duration of the first stage; calculating a modulation frequency as a function of the duration of the first stage; and applying an RF voltage at the RF voltage level calculated above for the duration of the second stage calculated above, and modulating the RF voltage by pulses at the modulation frequency calculated above.

In another embodiment of the present invention, a control method is provided for welding of biological tissue comprising: applying an increasing RF voltage, preferably increasing at a gradually decreasing rate, to the electrodes of a tissue welding tool during a first stage; measuring the values of the RF voltage and electric current passing through the tissue, and the duration of the first stage; calculating tissue impedance values by dividing the RF voltage values by the electric current values; determining a minimum tissue impedance value; storing the minimum tissue impedance value; calculating a relative tissue impedance value by dividing the tissue impedance values by the minimum tissue impedance value; stopping the first stage when the relative tissue impedance reaches an endpoint relative tissue impedance value calculated as a function of the relative tissue impedance; storing the duration of the first stage and a value of the RF voltage at the end of the first stage; calculating the duration of the second stage as a function of the duration of the first stage; and applying the RF voltage during the second stage, wherein the RF voltage is varied as a function of the relative tissue impedance during the second stage.

In another embodiment of the present invention, a control method is provided for welding of biological tissue comprising: applying an increasing RF voltage, preferably increasing at a gradually decreasing rate, to the electrodes of a tissue welding tool during a first stage; measuring the values of the RF voltage and electric current passing through the tissue; calculating tissue impedance values by dividing the RF voltage values by the electric current values; determining a minimum tissue impedance value; storing the minimum tissue impedance value; calculating relative tissue impedance values by dividing the tissue impedance values by the minimum tissue impedance values; stopping the first stage when the relative tissue impedance reaches an endpoint relative tissue impedance value calculated as a function of the relative tissue impedance; storing the duration of the first stage and a value of the RF voltage; calculating an initial RF voltage level for a second stage as a function of the value of the RF voltage at the end of the first stage; calculating the duration of the second stage as a function of the duration of the first stage; calculating a modulation frequency as a function of the duration of the first stage; and applying an RF voltage for the duration of the second stage calculated above, initially setting the amplitude of the RF voltage to the initial RF voltage level calculated above, modulating the RF voltage by pulses at the modulation frequency calculated above, and varying the amplitude of the RF voltage as a function of the relative tissue impedance.

Preferably the method further comprises stabilizing the relative tissue impedance during the second stage at the endpoint relative tissue impedance value. Stabilizing the relative tissue impedance is preferably performed by a regulatory system which stabilizes the relative tissue impedance by varying the RF voltage pulses by a predetermined amount, the RF voltage being varied based on the change of the relative tissue impedance. Preferably, the regulatory system stabilizes the relative tissue impedance by varying the RF voltage pulses by a predetermined amount starting with a calculated initial level.

Preferably the method further comprises varying the relative tissue impedance according to a preset method, this variation preferably being made by the regulatory system affecting the amplitude of the RF voltage pulses.

The present invention may be implemented with any combination of hardware and software. If implemented as a computer-implemented apparatus, the present invention is implemented using means for performing all of the steps and functions described above. The present invention can also be included in an article of manufacture (e.g., one or more computer program products) having, for instance, computer useable media. The media has embodied therein, for instance, computer readable program code means for providing and facilitating the mechanisms of the present invention. The article of manufacture can be included as part of a computer system or sold separately.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A method for welding of biological tissue comprising:
   (a) applying an RF voltage during a first stage to electrodes of a tissue welding tool;
   (b) monitoring tissue impedance, and determining a minimum tissue impedance value during the first stage;
   (c) determining relative tissue impedance, the relative tissue impedance being equal to the ratio of tissue impedance to the minimum tissue impedance value;
   (d) detecting when the relative tissue impedance reaches a predetermined relative tissue impedance value;
   (e) starting a second stage when the relative tissue impedance reaches the predetermined relative tissue impedance value;
   (f) calculating the duration of the second stage as a function of the duration of the first stage; and
   (g) applying the RF voltage during the second stage to the electrodes of the tissue welding tool.

2. The method of claim 1 wherein the amplitude of the RF voltage applied during the first stage increases according to the following equation:

$$U = u_s * t^k$$

where U is voltage, $u_s$ is a constant, t is time, and k is a constant, and where k<1.

3. The method of claim 1 wherein monitoring tissue impedance of step (b) comprises measuring the RF voltage and electric current between the electrodes of the tissue welding tool and calculating tissue impedance by dividing the voltage by the electric current.

4. The method of claim 1 wherein the predetermined relative tissue impedance value is calculated as a function of the RF voltage during the first stage.

5. The method of claim 1 wherein the predetermined relative tissue impedance value is within the range of about 1–1.5.

6. The method of claim 1 wherein the RF voltage applied during the second stage is calculated as a function of the value of the RF voltage applied during the first stage when the relative tissue impedance reaches the predetermined relative tissue impedance value.

7. The method of claim 1 wherein the RF voltage applied during the second stage is between about 50–100% of the value of the RF voltage applied at the end of the first stage.

8. The method of claim 1 wherein applying the RF voltage during the second stage comprises substantially stabilizing the RF voltage applied during the second stage.

9. The method of claim 1 further comprising modulating the RF voltages applied during the first and second stages by pulses.

10. The method of claim 9 wherein the pulses have a frequency of between about 100 Hz–60 kHz and a duty cycle of between about 10–90%.

11. The method of claim 9 wherein the frequency of the pulses is varied during the first and second stages.

12. The method of claim 1 further comprising modulating the RF voltages applied during the first and second stages with pulses having a frequency of between about 100 Hz–60 kHz, and further modulating the RF voltage applied during the second stage with low frequency pulses.

13. The method of claim 12 further comprising substantially stabilizing the amplitude of the RF voltage applied during the second stage, wherein the amplitude of the RF voltage is calculated as a function of the value of the RF voltage at the end of the first stage.

14. The method of claim 12 wherein the frequency of the low frequency pulses is defined as a function of the duration of the first stage.

15. The method of claim 12 wherein the frequency of the low frequency pulses is defined such that there are between about 5–10 pulses during the second stage.

16. The method of claim 1 wherein applying the RF voltage during the second stage comprises varying the RF voltage as a function of the relative tissue impedance.

17. The method of claim 16 further comprising substantially stabilizing the relative tissue impedance at a relative tissue impedance level reached at the end of the first stage.

18. The method of claim 16 wherein the RF voltage applied during the second stage is varied as a function of the relative tissue impedance by reducing the RF voltage when the relative tissue impedance is greater than the predetermined relative tissue impedance value and increasing the RF voltage when the relative tissue impedance is less than the predetermined relative tissue impedance value.

19. The method of claim 1 wherein applying the RF voltage during the second stage comprises varying the RF voltage to vary the relative tissue impedance according to a preset program.

20. The method of claim 1 further comprising modulating the RF voltages applied during the first and second stages with pulses having a frequency of between about 100 Hz–60 kHz, and further modulating the RF voltage applied during the second stage with low frequency pulses, and further comprising substantially stabilizing the relative tissue impedance at a relative tissue impedance level reached at the end of the first stage.

21. The method of claim 20 wherein the frequency of the low frequency pulses is defined as a function of the duration of the first stage.

22. The method of claim 20 wherein the frequency of the low frequency pulses is defined such that there are between about 5–10 pulses during the second stage.

23. The method of claim 20 wherein stabilizing the relative tissue impedance is performed by a regulatory system.

24. The method of claim 23 wherein the regulatory system stabilizes the relative tissue impedance by varying the RF voltage by a predetermined amount, the RF voltage being varied based on the direction of change of the relative tissue impedance.

25. The method of claim 1 further comprising modulating the RF voltages applied during the first and second stages with pulses having a frequency of between about 100 Hz–60 kHz, and further modulating the RF voltage applied during the second stage with low frequency pulses, and further comprising varying the RE voltage to vary the relative tissue impedance according to a preset program.

26. The method according to claim 25 wherein varying the relative tissue impedance is performed by a regulatory system.

27. The method of claim 1 further comprising monitoring tissue welding, and stopping tissue welding and providing a signal to a user if the RF voltage applied during the first stage reaches a preset RF voltage level and/or if the relative tissue impedance fails to reach the predetermined relative tissue impedance value.

28. The method of claim 1 further comprising monitoring tissue welding and stopping tissue welding and providing a signal to a user when the tissue impedance reaches a short circuit impedance of the electrodes of the tissue welding tool.

29. The method of claim 1 further comprising monitoring tissue welding and providing a signal to a user after tissue welding is completed at the end of the second stage and the welded tissue has sufficiently cooled.

30. A control method for welding of biological tissue comprising:
   (a) applying an increasing RF voltage to the electrodes of a tissue welding tool during a first stage;
   (b) measuring the values of the RF voltage and electric current passing through the tissue, and the duration of the first stage;
   (c) calculating tissue impedance values by dividing the RF voltage values by the electric current values;
   (d) determining a minimum tissue impedance value;
   (e) storing the minimum tissue impedance value;
   (f) calculating relative tissue impedance values by dividing of the tissue impedance values by the minimum tissue impedance value;
   (g) stopping the first stage when the relative tissue impedance reaches an endpoint relative tissue impedance value calculated as a function of the relative tissue impedance;
   (h) storing the duration of the first stage and a value of the RF voltage at the end of the first stage;
   (i) calculating an RF voltage level for a second stage as a function of the value of the RF voltage at the end of the first stage;
   (j) calculating the duration of the second stage as a function of the duration of the first stage; and (k) applying an RF voltage during the second stage at the RF voltage level calculated in step (i).

31. A control method for welding of biological tissue comprising:
   (a) applying an increasing RF voltage to the electrodes of a tissue welding tool during a first stage;
   (b) measuring the values of the RF voltage and electric current passing through the tissue, and the duration of the first stage;
   (c) calculating tissue impedance values by dividing the RF voltage values by the electric current values;
   (d) determining a minimum tissue impedance value;
   (e) storing the minimum tissue impedance value;
   (f) calculating relative tissue impedance values by dividing the tissue impedance values by the minimum tissue impedance value;
   (g) stopping the RF voltage increase when the relative tissue impedance reaches an endpoint relative tissue impedance value calculated as a function of the relative tissue impedance;
   (h) storing the duration of the first stage and the RF voltage at the end of the first stage;
   (i) calculating an RF voltage level for a second stage as a function of the value of the RF voltage at the end of the first stage;
   (j) calculating the duration of the second stage as a function of the duration of the first stage;
   (k) calculating a modulation frequency as a function of the duration of the first stage; and
   (l) applying an RF voltage at the RF voltage level calculated in step (i) for the duration of the second stage calculated in step (j), and modulating the RF voltage by pulses at the modulation frequency calculated in step (k).

32. A control method for welding of biological tissue comprising:
   (a) applying an increasing RF voltage to the electrodes of a tissue welding tool during a first stage;
   (b) measuring the values of the RF voltage and electric current passing through the tissue, and the duration of the first stage;
   (c) calculating tissue impedance values by dividing the RF voltage values by the electric current values;
   (d) determining a minimum tissue impedance value;
   (e) storing the minimum tissue impedance value;
   (f) calculating relative tissue impedance values by dividing the tissue impedance values by the minimum tissue impedance value;
   (g) stopping the first stage when the relative tissue impedance reaches an endpoint relative tissue impedance value calculated as a function of the relative tissue impedance;
   (h) storing the duration of the first stage and value of the RF voltage at the end of the first stage;
   (i) calculating the duration of the second stage as a function of the duration of the first stage; and
   (j) applying the RF voltage during the second stage, wherein the RF voltage is varied as a function of the relative tissue impedance during the second stage.

33. A control method for welding of biological tissue comprising:
   (a) applying an increasing RF voltage to the electrodes of a tissue welding tool during a first stage;
   (b) measuring the values of the RF voltage and electric current passing through the tissue, and the duration of the first stage;
   (c) calculating tissue impedance values by dividing the RF voltage values by the electric current values;
   (d) determining a minimum tissue impedance value;
   (e) storing the minimum tissue impedance value;
   (f) calculating relative tissue impedance values by dividing the tissue impedance values by the minimum tissue impedance value;
   (g) stopping the first stage when the relative tissue impedance reaches an endpoint relative tissue impedance value calculated as a function of the relative tissue impedance;
   (h) storing the duration of the first stage and a value of the RF voltage at the end of the first stage;
   (i) calculating an initial RF voltage level for a second stage as a function of the value of the RF voltage at the end of the first stage;
   (j) calculating the duration of the second stage as a function of the duration of the first stage;
   (k) calculating a modulation frequency as a function of the duration of the first stage; and
   (l) applying an RF voltage for the duration of the second stage calculated in step (j), initially setting the amplitude of the RF voltage to the initial RF voltage level calculated in step (i), modulating the RF voltage by pulses at the modulation frequency calculated in step (k), and varying the amplitude of the RF voltage as a function of the relative tissue impedance.

34. The method of claim 33 further comprising stabilizing the relative tissue impedance at the endpoint relative tissue impedance value.

35. The method of claim 34 wherein stabilizing the relative tissue impedance is performed by a regulatory system which stabilizes the relative tissue impedance by varying the amplitude of the RF voltage by a predetermined amount, the RF voltage being varied based on the direction of change of the relative tissue impedance.

36. The method of claim 33 wherein varying the RF voltage of step (l) comprises varying the RF voltage to vary the relative tissue impedance according to a preset program.

* * * * *

UNITED STATES PATENT AND TRADEMARK OFFICE
CERTIFICATE OF CORRECTION

PATENT NO. : 6,733,498 B2
DATED : May 11, 2004
INVENTOR(S) : Boris E. Paton et al.

It is certified that error appears in the above-identified patent and that said Letters Patent is hereby corrected as shown below:

<u>Column 4,</u>
Line 4, delete "(shown in FIGS. 3, 5, and 6 as value A)" and insert (-- shown in FIG. 3 as value A) --

<u>Column 5,</u>
Lines 6-7 and 31, delete "(shown in FIG. 5 as A)" and insert -- (shown in FIG. 5as D) -- therein;

<u>Column 7,</u>
Line 3, delete "1-5" and insert -- 1-1.5 -- therein;
Line 26, delete "The pulses preferably" and insert -- The pulses are preferably -- therein;

<u>Column 12,</u>
Line 22, delete "the RE voltage" and insert -- the RF voltage -- therein;

<u>Column 14,</u>
Line 5, delete "of step (I) comprises" and insert -- of step (1) comprises --therein.

Signed and Sealed this

Seventeenth Day of August, 2004

JON W. DUDAS
*Acting Director of the United States Patent and Trademark Office*